(12) United States Patent
Balkus, Jr. et al.

(10) Patent No.: US 9,216,198 B2
(45) Date of Patent: Dec. 22, 2015

(54) COMPOSITIONS AND MEDICAL DEVICES FOR CONTROLLED RELEASE OF NITRIC OXIDE AND METHODS OF PRODUCTION THEREOF

(75) Inventors: Kenneth J. Balkus, Jr., The Colony, TX (US); Harvey A. Liu, Houston, TX (US)

(73) Assignee: THE BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 636 days.

(21) Appl. No.: 12/750,317

(22) Filed: Mar. 30, 2010

(65) Prior Publication Data

US 2010/0285100 A1 Nov. 11, 2010

Related U.S. Application Data

(60) Provisional application No. 61/164,769, filed on Mar. 30, 2009.

(51) Int. Cl.
| | |
|---|---|
| *A61K 33/00* | (2006.01) |
| *A61K 47/48* | (2006.01) |
| *A61K 33/24* | (2006.01) |
| *A61K 41/00* | (2006.01) |
| *B82Y 5/00* | (2011.01) |
| *B82Y 30/00* | (2011.01) |
| *C01G 21/21* | (2006.01) |
| *C01G 23/047* | (2006.01) |

(52) U.S. Cl.
CPC .............. *A61K 33/24* (2013.01); *A61K 33/00* (2013.01); *A61K 41/0042* (2013.01); *A61K 47/48861* (2013.01); *B82Y 5/00* (2013.01); *B82Y 30/00* (2013.01); *C01G 21/21* (2013.01); *C01G 23/047* (2013.01); *C01P 2002/82* (2013.01); *C01P 2004/04* (2013.01); *C01P 2004/13* (2013.01)

(58) Field of Classification Search
USPC ........................................................ 424/718
See application file for complete search history.

(56) References Cited

U.S. PATENT DOCUMENTS

| | | | | |
|---|---|---|---|---|
| 2002/0094985 | A1* | 7/2002 | Herrmann et al. | 514/245 |
| 2006/0269620 | A1* | 11/2006 | Morris et al. | 424/684 |
| 2007/0014947 | A1* | 1/2007 | Mengel et al. | 428/34.1 |
| 2007/0203564 | A1* | 8/2007 | Rusk et al. | 623/1.13 |

\* cited by examiner

*Primary Examiner* — Michael B Pallay
(74) *Attorney, Agent, or Firm* — Saliwanchik, Lloyd & Eisenschenk

(57) ABSTRACT

The present disclosure describes compositions providing for controlled release of nitric oxide (NO) and methods for production of these compositions. In some embodiments, the compositions may include a biodegradable polymer and a nitric oxide-releasing material at least partially encapsulated by the biodegradable polymer. Nitric oxide-releasing materials may include, for example, diazeniumdiolates and nitric oxide contained within a zeolite, metal-organic framework or other porous material. In general, the compositions are spun into a porous fiber, which may be further annealed by heating in order to densify the fiber. Annealing may prolong the NO release profile. Medical devices containing the compositions described herein are also contemplated by the present disclosure. Medical devices include, for example, textiles, bandages and articles of clothing.

22 Claims, 7 Drawing Sheets

○ NO-RELEASING MATERIAL
□ BIODEGRADABLE POLYMER

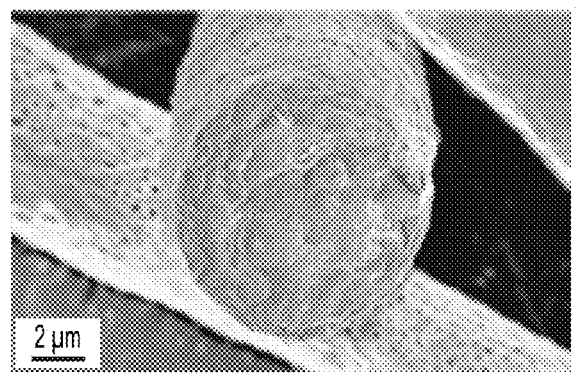
FIG. 8
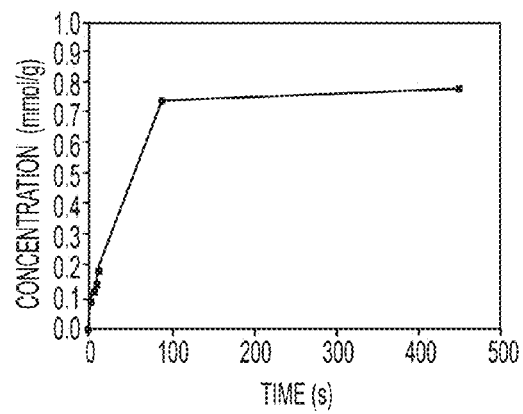
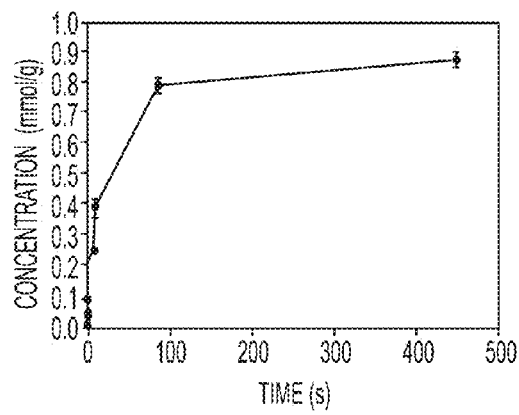
FIG. 9A          FIG. 9B
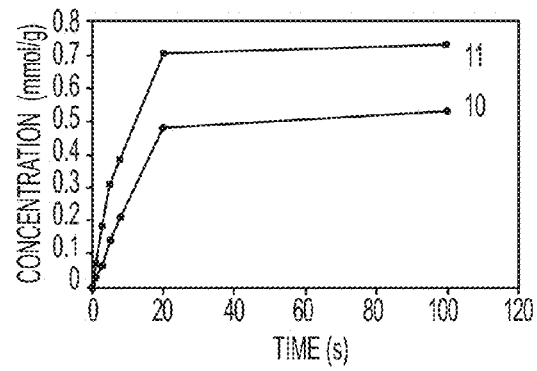
FIG. 10

* BANDAGE APPLIED AND FLOW WAS STABILIZED BEFORE
SUBSEQUENT MEASUREMENTS WERE TAKEN

COMPOSITIONS AND MEDICAL DEVICES FOR CONTROLLED RELEASE OF NITRIC OXIDE AND METHODS OF PRODUCTION THEREOF

CROSS-REFERENCE TO RELATED APPLICATIONS

This application claims priority to U.S. provisional patent application 61/164,769, filed Mar. 30, 2009, which is incorporated by reference herein in its entirety.

STATEMENT REGARDING FEDERALLY-SPONSORED RESEARCH

Not applicable.

BACKGROUND

Nitric oxide (NO) has long been established as a signaling molecule that promotes relaxation of smooth muscle cells. More recently, it has been established that NO can mediate other biological processes and diseases including, for example, wound healing, inflammation, plant disease resistance, sexual dysfunction, social dysfunction, cancer, coronary heart disease, restenosis, hypertension and angiogensis. The implication of NO in so many biological processes and diseases has stimulated interest in its exogenous delivery. However, NO is a diatomic free radical, and its exogenous delivery as a gas to biological systems has proved impractical due to its high reactivity.

A number of systems have been proposed and tested for in situ generation and delivery of NO. Such systems include chemical compounds such as, for example, diazeniumdiolates and S-nitrosothiols. Other examples include, NO-releasing gold nanoparticles, NO-releasing polyethyleneimine (PEI) fibers and NO-releasing zeolites. Diazeniumdiolates and zeolites are materials that hold particular promise for in situ generation of NO. However, neither of these systems has yet been successfully implemented in a controlled-release formulation that provides a sustained generation of NO over an extended period. Further, efforts to formulate diazeniumdiolates within a polymer matrix have been hampered by leaching of these hydrophilic molecules from the matrix. Leached diazeniumdiolates may become toxic in vivo due to metabolic conversion to N-nitrosamines, which are potentially carcinogenic materials.

Zeolites are open, stable, three-dimensional microporous aluminosilicates composed of ordered tetrahedra of $AlO_4$ and $SiO_4$. These materials have experienced a growing interest for biomedical applications. Zeolites are the aluminosilicate members of the family of microporous solids known as "molecular sieves." With regard to in situ delivery of NO, they have shown exceptional promise for their ability to store and reversibly release NO from their microporous structure. In spite of their ability to readily store NO, application of NO-loaded zeolites and other porous materials as a free powder to biological systems is generally not considered practical.

In view of the foregoing, new biocompatible systems for controlled or sustained release of NO would be of substantial benefit. Desirably, such systems would promote controlled or sustained release of NO to exploit the desirable properties of NO in biological systems, while at the same time minimizing the toxicity or biological incompatibility of the NO-releasing material. Biocompatible systems for controlled or sustained release of NO may be incorporated into medical devices as described herein.

SUMMARY

In various embodiments, the present disclosure describes compositions for controlled release of nitric oxide. The compositions include a biodegradable polymer and a nitric oxide-releasing material at least partially encapsulated by the biodegradable polymer.

In other various embodiments, compositions for controlled release of nitric oxide include a biodegradable polymer and a nitric oxide-releasing material at least partially encapsulated by the biodegradable polymer. The nitric oxide-releasing material is nitric oxide contained within a porous material. The porous material may be, for example, a zeolite, metal-organic framework or mesoporous molecular sieve.

Examples of mineral zeolites include, for example, analcime ($NaAlSi_2O_6 \cdot H_2O$), chabazite [$(Ca,Na_2,K_2,Mg)Al_2Si_4O_{12} \cdot 6H_2O$], clinoptilolite [$(Na,K,Ca)_{2-3}Al_3(Al,Si)_2Si_{13}O_{36} \cdot 12(H_2O)$], heulandite [$(Ca,Na)_{2-3}Al_3(Al,Si)_2Si_{13}O_{36} \cdot 12H_2O$], natrolite ($Na_2Al_2Si_3O_{10} \cdot 2H_2O$), phillipsite [$(Ca,Na_2,K_2)_3Al_6Si_{10}O_{32} \cdot 12H_2O$], and stilbite ($NaCa_2Al_5Si_{13}O_{36} \cdot 14H_2O$). Examples of mesoporous molecular sieves include, for example, MCM-41 and SBA-15. By virtue of their porous structure, zeolites can accommodate a wide variety of cations, such as $Na^+$, $K^+$, $Ca^{2+}$, $Mg^{2+}$ and others. These positive ions are rather loosely held and can readily be exchanged for other cations in a contact solution. In certain embodiments herein, metal-exchanged zeolites may be used as the porous material, wherein the metal is a transition metal. Preferred transition metals include, but are not limited to, Ti, V, Mn, Fe, Co, Cr, Zr, Nb, Mo, and W.

The porous material can also be a metal-organic framework (MOF), which is a crystalline compound containing metal ions or clusters coordinated to often rigid organic molecules to form one-, two-, or three-dimensional structures that can be porous. A metal-organic framework (MOF) is composed of a metal ion or cluster of metal ions and an organic molecule called a linker. The choice of metal and linker has significant influence on the structure and properties of the MOF in that the metal's coordination preference influences the size and shape of pores by dictating how many ligands can bind to the metal and in which orientation. Example of MOFs include, for example, carboxylate-based MOFs, heterocyclic azolate-based MOFs, metal-cyanide MOFs, covalent organic frameworks and zeolite imidazolite frameworks.

In certain embodiments, S-nitrosothiol compounds encapsulated in zeolites can be used as the source of NO, rather than adsorbed NO gas. S-nitrosothiols are a group of NO donors that can be designed to release NO at varying rates. The infinite flexibility of NO release from porous materials such as zeolites, mesoporous molecular sieves and metal-organic frameworks allows the development of a wide range of different NO donor materials.

In some embodiments, the present disclosure includes methods for preparing compositions for controlled release of nitric oxide. The methods include providing a polymer solution of a biodegradable polymer dissolved in a solvent; dispersing a nitric oxide-releasing material into the polymer solution; and electrospinning the polymer solution into a fiber containing pores.

In other various embodiments, the methods for preparing compositions for controlled release of nitric oxide include providing a polymer solution of a biodegradable polymer dissolved in a solvent; dispersing a porous material in the polymer solution; electrospinning the polymer solution into a fiber containing pores; and impregnating the porous material with nitric oxide. The porous material may be, for example, a zeolite or a metal-organic framework. In some embodiments, the methods further include annealing the fiber by heating after impregnating the zeolite with nitric oxide.

In still other various embodiments, the present disclosure describes medical devices containing compositions for controlled release of nitric oxide.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIG. 8 shows an illustrative cross-sectional SEM image of a cobalt (II)-exchanged Zeolite-A-containing fiber following NO loading and annealing;

FIG. 9A shows an illustrative NO release profile from NO-loaded cobalt (II)-exchanged Zeolite-A; FIG. 9B shows an illustrative NO release profile from NO-loaded cobalt (II)-exchanged nanoscale Zeolite-A;

FIG. 10 shows illustrative NO release profiles from non-annealed, porous fibers containing cobalt (II)-exchanged Zeolite-A and cobalt (II)-exchanged nanoscale Zeolite-A;

DETAILED DESCRIPTION

Figure 1:
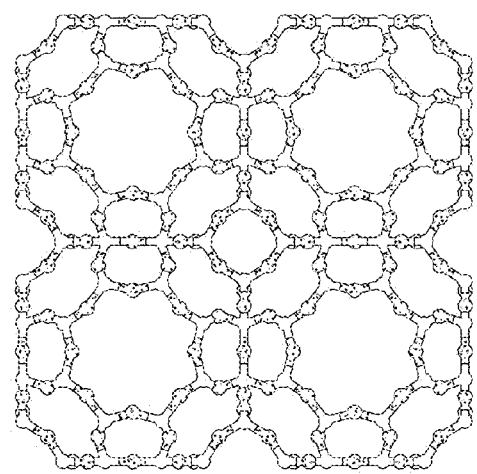
FIG. 1 shows the structure of Zeolite-A.

In the following description, certain details are set forth such as specific quantities, sizes, etc. so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. Drawings are not necessarily to scale.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not, unless specifically stated in this specification or if the incorporation is necessary for maintaining validity.

As used herein, the term "biodegradable polymer" refers to, for example, a polymer which at least partially degrades to its constituent monomers when exposed to aqueous conditions.

As used herein, the term "nitric oxide-releasing material" refers to, for example, a material that either releases adsorbed or occluded nitric oxide upon exposure to specified conditions or releases nitric oxide through a chemical reaction upon exposure to specified conditions.

As used herein, the term "medical device" refers to, for example, any device used either internally or externally for treating, mediating, curing or alleviating a condition in a patient or any device used as part of a medical procedure.

Mammalian cells synthesize NO using a two-step enzymatic process that oxidizes L-arginine to N-omega-hydroxy-L-arginine, which is subsequently converted into L-citrulline and an uncharged NO free radical. Three different nitric oxide synthase enzymes regulate NO production. Neuronal nitric oxide synthase (NOS1 or nNOS) is formed within neuronal tissue and plays a role in neurotransmission. Endothelial nitric oxide synthase (NOS3 or eNOS) is secreted by endothelial cells and induces vasodilatation. Inducible nitric oxide synthase (NOS2 or iNOS) is principally found in macrophages, hepatocytes and chondrocytes and is associated with immune cytotoxicity. Neuronal NOS and eNOS are constitutive enzymes that regulate the rapid, short-term release of small amounts of NO. In these minute amounts NO activates guanylate cyclase, which elevates cyclic guanosine monophosphate (cGMP) concentrations, which in turn increase intracellular $Ca^{2+}$ levels. Increased intracellular $Ca^{2+}$ levels result in smooth muscle relaxation and vasodilation effects.

Inducible NOS is responsible for the sustained release of larger amounts of NO and is activated by extracellular factors including endotoxins and cytokines. These higher NO levels play a role in cellular immunity.

Nitric oxide's therapeutic potential has been studied in a number of diverse clinical indications including, for example, cancer, coronary artery heart disease, restenosis, hypertension, angiogenesis, sexual dysfunction and social dysfunction. Moreover, recent studies have demonstrated that NO also possesses considerable in vivo and ex vivo antimicrobial activity, suggesting a possible role in treating infectious diseases and fungal infections. The role of NO in wound healing and general inflammation has also been studied.

Another postulated clinical role of NO is in the field of organ transplantation, particularly heart transplantation. One of the major factors in realizing a successful heart transplantation is adequate organ preservation during the procurement, storage, and implantation stages of a transplant. Currently, organ preservation is based on a single flush induction of cardioplegia and hypothermic storage in a solution. While this method is effective, time is still the major factor in healing, because the heart can only tolerate 4-5 hours of ischemia. Prolonged periods of ischemia lead to increased acute and chronic organ failure due to vasoconstriction and endothelium damage of the arteries upon a decrease in NO production.

Attempts to mimic the natural release of NO produced by NOS enzymes have yet to be successful. Embodiments of the present disclosure seek to provide compositions permitting the controlled or sustained release of NO in a manner that is substantially non-toxic to biological systems and/or successfully mimics the natural enzymatic release of NO. In view of the established role of NO in so many biological processes, such compositions would demonstrate substantial utility in the art. Medical devices and other therapeutic devices that contain such compositions are also contemplated herein.

In various embodiments, the present disclosure describes compositions for controlled release of nitric oxide. The compositions include a biodegradable polymer and a nitric oxide-releasing material at least partially encapsulated by the biodegradable polymer.

The nitric oxide-releasing material may be either a material that releases adsorbed or occluded nitric oxide upon exposure to specified conditions or a material that releases nitric oxide through a chemical reaction upon exposure to specified conditions. Nitric oxide may be released from such compounds under physiological conditions, including exposure to an aqueous environment. Nitric oxide release may also occur through biochemical processes mediated by enzymes and co-factors. For enzymatic conversion, enzyme levels and co-factors required to stimulate NO production are often depleted after repeat usage, and there is typically a physiological recovery window of about 10 to 12 hours for administration of such enzymatically-activated compounds.

Nitric oxide-releasing materials that produce nitric oxide through a chemical reaction may be considered nitric oxide prodrugs. Nitric oxide prodrugs may include, for example, organic N-nitro and N-nitroso compounds (for example, diazeniumdiolates), organic O-nitro and O-nitroso compounds (for example, glyceryl trinitrate and amyl nitrite), organic C-nitro and C-nitroso compounds (for example, nitrolipids, nitronic acids, nitroalkanes, diazetine dioxides and furoxans), S-nitrosophenols, S-nitrosothiols, N-hydroxyurea and derivatives, N-hydroxyguanidine and derivatives, and nitroprusside ion and other metal nitrosyl complexes.

Among these nitric oxide-releasing materials, diazeniumdiolates are the most extensively studied. The general structural formula of diazeniumdiolates is exemplified by structure I below, where R and R' are independently H or any alkyl, alkenyl, alkynyl, aryl, aralkyl, alkaryl group or substituted derivative thereof. Charge balance is generally affected by a monovalent cation such as, for example, a $Na^+$ cation.

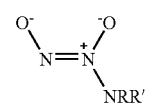

Diazeniumdiolates have half-lives for NO release generally ranging from about 2 seconds to about 20 hours depending on their R and R' substitution. NO release is stimulated by the exposure of the diazeniumdiolate to protic conditions. In various embodiments of the present disclosure, the nitric oxide-releasing material is a diazeniumdiolate.

In other various embodiments of the present disclosure, the nitric oxide-releasing material is a material that releases adsorbed or occluded nitric oxide upon exposure to specified conditions. Materials meeting this criterion include porous materials such as, for example, zeolites, metal-exchanged zeolites, metal-organic frameworks, and mesoporous molecular sieves.

Zeolites have shown the capability to reversibly bind and release NO. Zeolite-A (also known in the art as LTA zeolite), in particular, has shown a particular capability for facile adsorption and release of nitric oxide. FIG. 1 shows the structure of Zeolite-A. The structure includes channels having an opening of about 4 Å in width. Exchangeable $Na^+$ cations (not shown) are found within the channels of the zeolite structure. Nitric oxide adsorption may be improved by altering the type and amount of cations contained within the zeolite structure. Suitable cations may be introduced through a simple ion exchange with the $Na^+$ cations in the channels. In various embodiments, the metal exchanged for the $Na^+$ cation may be a transition metal or lanthanide metal. Co (II)-exchanged Zeolite-A is particularly efficacious at adsorbing nitric oxide, with a maximum adsorption capacity of about 1.7 mmol NO/g zeolite. Nitric oxide release may be affected by exposure of the NO-containing zeolite to atmospheric moisture or water. In various embodiments of the present compositions, the nitric oxide-releasing material is nitric oxide contained within a zeolite. In some embodiments, the zeolite is Zeolite-A. In some embodiments, the zeolite is cobalt (II)-exchanged Zeolite-A. One of ordinary skill in the art will recognize that any zeolite or metal-exchanged zeolite that reversibly binds NO may be used equivalently within the spirit and scope of the present disclosure.

In some embodiments, the porous, nitric oxide-releasing material may be a metal-organic framework. An illustrative metal-organic framework for reversible binding of NO described herein is a copper (II) biphenyl-4,4'-dicarboxylic acid triethylenediamine metal-organic framework nanocrystals. Metal-organic frameworks also include zeolite-imidazolate MOFs, carboxylate-based MOFs, heterocyclic azolate-based MOFs, metal-cyanide MOFs, and covalent organic frameworks In addition to the aforesaid embodiments, porous materials may also contain compounds operable for release of nitric oxide. In such embodiments, the porous materials release nitric oxide through a chemical reaction rather than through release of adsorbed nitric oxide. In an embodiment, a S-nitrosothiol or a metal nitrosyl complex may be housed within a porous material such as a zeolite or a metal-organic framework material.

Biodegradable polymers suitable for the compositions of the present disclosure are not particularly limited. Such biodegradable polymers may include any polymer that at least partially depolymerizes under physiological or aqueous conditions. Illustrative biodegradable polymers include, for example, poly(lactic acid) (D and L forms), polycaprolactone, poly(glycolic acid), polylactide (PLA), polydioxanone, polyglycolide (PGA), polyanhydrides, polyorthoesters, poly (amino acids), chitosans and sulfonated chitosan. Mixtures of biodegradable polymers and various co-polymers of the biodegradable polymers are also included within the spirit and scope of the present disclosure. Naturally-occurring biodegradable polymers may include, for example, reconstituted collagen, starch, or natural silks. Water-soluble polymers such as, for example, poly(vinyl pyrrolidone) (PVP), poly (ethylene oxide) (PEO), poly(vinyl alcohol) (PVA), and poly (acrylic acid) (PAA) may be mixed with the aforesaid biodegradable polymers in various embodiments of the present disclosure. The amount of water-soluble polymer mixed with the biodegradable polymer may range from about 1% by weight to about 99% by weight.

In various embodiments of the compositions described herein, the biodegradable polymer is poly(lactic acid). Poly (lactic acid) is a known constituent of drug delivery compositions and is considered to be non-toxic. Its hydrolysis product, lactic acid, is commonly produced in mammalian organisms. Further, poly(lactic acid) has also been implicated to facilitate transepidermal delivery of drugs. Hence, compositions of the present disclosure may be used either internally or externally for delivery of nitric oxide to a target tissue. The above advantages of poly(lactic acid) notwithstanding, one of ordinary skill in the art will recognize that any biodegradable polymer having suitable properties may be used in the various embodiments of the present disclosure, and the aforesaid listing of biodegradable polymers should not be construed as limiting of the scope of the present disclosure.

In various embodiments of the compositions described herein, the biodegradable polymer contains pores. In some embodiments, a portion of the composition contains pores and the remainder of the composition does not contain pores. In other embodiments, the entire composition is substantially porous. In some embodiments, at least a portion of the nitric oxide-releasing material is located within the pores. In some embodiments, the pores form a tortuous pathway within the composition. Such tortuous pathways limit the accessibility of moisture and chemical reagents to interior portions of the compositions, thereby slowing the release of nitric oxide from the nitric oxide-releasing materials contained therein. In some embodiments, the nitric oxide-releasing material located within the pores is a diazeniumdiolate. Advantages of a diazeniumdiolate at least partially encapsulated within the pores of biodegradable polymer are discussed hereinafter.

In various embodiments of the compositions described herein, the biodegradable polymer is spun into fibers. A plurality of the fibers may be combined, spun or assembled into a free-standing paper or fabric. In some embodiments, the fibers have diameters ranging from about 100 nm to about 25 µm. In other embodiments, the fibers have diameters ranging from about 500 nm to about 25 µm or from about 1 µm to about 25 µm or from about 1 µm to about 100 µm. In some embodiments, the fibers have diameters of less than about 100 nm. In some embodiments, the fibers contain pores. In some embodiments, the entire fiber is substantially porous. In other embodiments, a portion of the fiber contains pores and the remainder of the fiber does not contain pores. In some embodiments, the exterior of the fiber contains pores, and the interior portions of the fiber are substantially non-porous.

In various embodiments, compositions of the present disclosure may be spun into fibers by an electrospinning technique. Electrospinning involves the introduction of an external electrostatic field to a conducting fluid being extruded through a needle. When the electric field is in equilibrium with the droplets being extruded through the needle, a suspended conical droplet, also known as a Taylor cone, is formed. Additional voltage causes the electric field to exceed the surface tension, thereby causing the droplet to become unstable and resulting in the ejection of a tiny fluid jet from the surface of the droplet. When the droplet contains a polymer, as in the embodiments of the present disclosure, ejection of the fluid jet results fiber formation. The elongated melt of the fluid jet experiences a whipping motion that results in polymer stretching during formation of the fibers. The fibers are collected on a grounded target as they are formed. In embodiments of the present disclosure, the fibers spun by electrospinning typically have a porous morphology due to phase separation of the biodegradable polymer from the solvent during spinning Rapid solvent evaporation thereby results in pore formation. Electrospinning apparatuses capable of forming sheets of fabric or free-standing papers of the compositions of the present disclosure are commercially available.

In embodiments wherein the nitric oxide-releasing material is a diazeniumdiolate, the compositions of the present disclosure may prove advantageous over those previously described in the art. Diazeniumdiolates function through a proton-mediated release of NO under physiological conditions. During NO release, the pH increases as a result of amine formation, which reduces the availability of protons to initiate further production of NO. Hence, the NO release rate of diazeniumdiolates is self-inhibited by increased pH, and to maintain a relatively constant NO release rate, external pH control generally needs to be performed. Furthermore, without pH regulation, only a small fraction of the theoretical amount of NO is produced.

Embodiments of the present disclosure advantageously overcome the self-inhibiting properties of diazeniumdiolates to afford a more constant NO release rate. In various embodiments of the present disclosure, the biodegradable polymer is hydrolysable in an aqueous solution, and a monomer produced by the hydrolysis of the biodegradable polymer is operable for buffering the aqueous solution. For example, in various embodiments of the present disclosure, the biodegradable polymer poly(lactic acid) hydrolyses to lactic acid. Lactic acid, in turn, can neutralize amines formed from the diazeniumdiolate, thereby buffering the aqueous solution at a pH more amenable for further NO release. Embodiments herein may also be effective at mitigating the toxic effects of diazeniumdiolate N-nitrosamine metabolic products.

Figure 2:
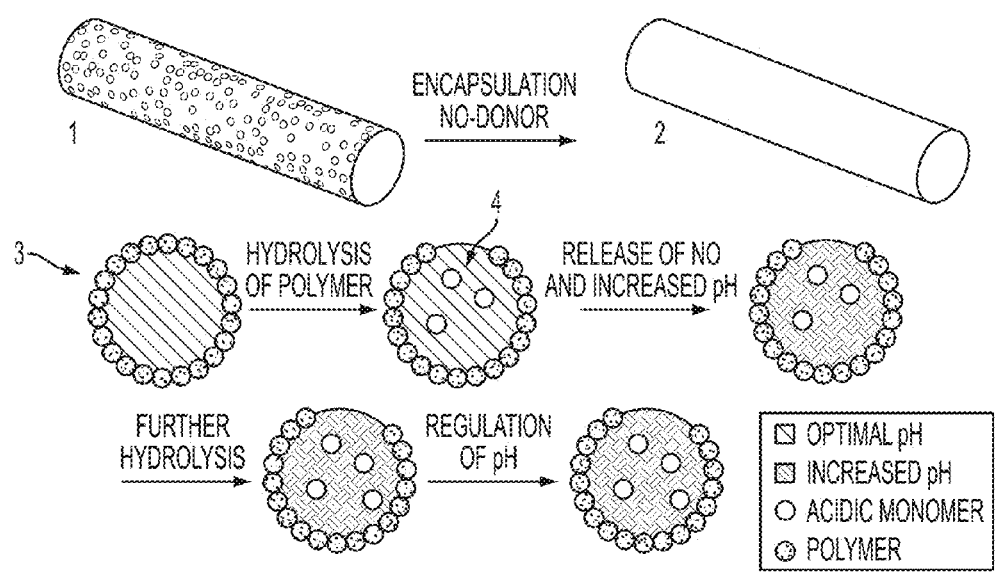
FIG. 2 shows an illustrative schematic demonstrating the manner in which poly(lactic acid) may buffer an aqueous solution during nitric oxide release from a diazeniumdiolate.

FIG. 2 shows an illustrative schematic demonstrating the manner in which poly(lactic acid) may buffer an aqueous solution during nitric oxide release from a diazeniumdiolate. As shown in FIG. 2, a porous poly(lactic acid) fiber 1 may be impregnated a diazeniumdiolate in order to encapsulate the diazeniumdiolate. A fiber 2 containing encapsulated diazeniumdiolate is formed. Encapsulating may involve annealing or coating fiber 2 after impregnating fiber 1 with the diazeniumdiolate. After encapsulating, at least a portion of the diazeniumdiolate is located within the pores of the fiber 2. The diazeniumdiolate contained within the pores constitutes many independent reservoirs of the nitric oxide-releasing material that are encapsulated by the poly(lactic acid) polymer. As shown in FIG. 2, upon hydrolysis of polymer 3, acidic monomers 4 are released which decrease the pH and buffer the solution within the pore. Concurrently, as polymer 3 is hydrolyzed, the diazeniumdiolate is exposed to protic conditions, resulting in NO and amine release. As further polymer 3 is hydrolyzed, more acidic monomers 4 are released to neutralize the amines produced. Since each pore serves as an independent reservoir of the diazeniumdiolate, NO release can be significantly prolonged beyond that typically observed in the absence of a polymer.

It should be understood that the buffering mechanism proposed in FIG. 2 is mechanistically non-limiting and represents Applicants' current understanding of the process by which NO is produced. Further, one of ordinary skill in the art will recognize that other nitric oxide-releasing materials may be substituted for a diazeniumdiolate in the embodiments described herein without departing from the spirit and scope of the present disclosure.

Like the diazeniumdiolates described hereinabove, in some embodiments of the present disclosure, at least a portion of the zeolites, metal-organic frameworks or other porous materials containing nitric oxide may be located within the pores of a biodegradable polymer fiber. In additional embodiments, the zeolite or metal-organic frameworks may be dispersed uniformly throughout the biodegradable polymer in the compositions described herein. In some embodiments, the pores of a biodegradable polymer fiber form a tortuous pathway connecting at least a portion of the zeolites.

Figure 3A:
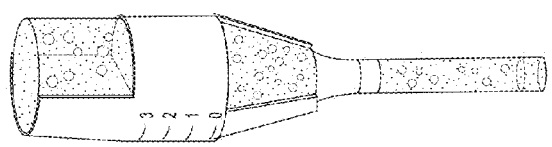
FIG. 3A shows an illustrative schematic of a standard electrospinning process in which a nitric oxide-releasing material is dispersed in a biodegradable polymer.
Figure 3B:
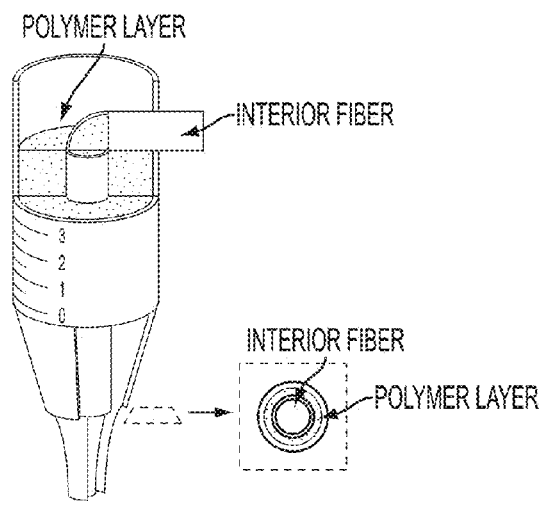
FIG. 3B shows an illustrative schematic of a concentric electrospinning process in which an interior fiber containing a biodegradable polymer and a nitric oxide-releasing material is coated with a polymer layer not containing the nitric oxide-releasing material.

Combining a biodegradable polymer with a zeolite, metal-organic framework or other porous material containing nitric oxide introduces an ability to tune the nitric oxide release characteristics through tailoring the porous morphology of the fiber. For example, in various embodiments of the present disclosure, the fiber may be annealed by heating so as to reduce the porosity of the fiber. Annealing may reduce the porosity of the interior portions of the fiber. Nitric oxide release characteristics may also be altered by modifying at least one property of the encapsulated zeolites including, for example, zeolite type, exchanged cation and zeolite channel diameter. Likewise, nitric oxide release may be modified by using various types of metal-organic frameworks or other porous materials identified hereinabove. In some embodiments of the present compositions, the nitric oxide release rate may be modified by coating the biodegradable polymer with a polymer layer that does not contain the nitric oxide-releasing material. FIG. 3A shows an illustrative schematic of a standard electrospinning process in which a nitric oxide-releasing material is dispersed in the biodegradable polymer. FIG. 3B shows an illustrative schematic of a concentric electrospinning process in which an interior fiber containing a biodegradable polymer and a nitric oxide-releasing material is coated with a polymer layer not containing the nitric oxide-releasing material. By controlling the thickness and identity of the polymer layer in the concentric electrospinning process, nitric oxide release rates may be adjusted as required by a particular application. In some embodiments, the polymer layer may be a biodegradable polymer that is the same or different than the biodegradable polymer containing the nitric oxide-releasing material.

Concentrations of the zeolite or metal-organic framework in the biodegradable polymer are only limited by the apparatus used for spinning fibers of the compositions described herein. High concentrations of zeolite or metal-organic framework in the biodegradable polymer may interfere with fiber formation. However, such operational limitations may be overcome through use of industrial scale fiber-spinning apparatuses, and all concentrations of porous materials within the fibers lie within the spirit and scope of the present disclosure. In some embodiments, a concentration of the zeolite in the biodegradable polymer is less than about 0.13 grams of zeolite per gram of biodegradable polymer.

In other various embodiments of the present disclosure, compositions for controlled release of nitric oxide include a biodegradable polymer and a nitric oxide-releasing material at least partially encapsulated by the biodegradable polymer. The nitric oxide-releasing material is nitric oxide contained within a porous material. The porous material may be, for example, a zeolite, a metal-organic framework, or a mesoporous molecular sieve. In some embodiments, the compositions release nitric oxide for at least about 6 hours. In other embodiments, the compositions release nitric oxide for at least about 3 hours, or at least about 12 hours, or at least about 24 hours, or at least about 48 hours. In some embodiments, the compositions release nitric oxide for more than 48 hours. In some embodiments, the biodegradable polymer is spun into fibers and the fibers have been annealed so as to reduce their porosity. Such annealing may enable more prolonged nitric oxide release.

Compositions of the present disclosure may be included with medical devices. In some embodiments of the medical devices, the nitric oxide-releasing material of the composition is a diazeniumdiolate. In other embodiments of the medical devices, the nitric oxide-releasing material of the composition is nitric oxide contained within a zeolite. In still other embodiments of the medical devices, the composition is nitric oxide contained within a metal-organic framework. In some embodiments, the composition coats the surface of the medical device. In such embodiments, the medical device may be implanted in a tissue or specifically placed externally in order to deliver its nitric oxide in a specific manner. The medical devices of the present disclosure may be manufactured from a material such as, for example, metal, glass, ceramic, fabrics and polymers upon or with which the compositions described herein may be deposited or admixed.

Medical devices of the present disclosure include stents, vascular grafts, pacemaker leads, heart valves, electrodes, sensors, trocars, guide wires, catheters, ocular lenses, sling materials, sutures, wound dressings and bandages, blood collection bags and storage tubes, tubing for blood transfusions and hemodialysis, diabetic socks and bedding. In some embodiments, the medical device is a bandage or wrap. In some embodiments, the medical device is a textile.

In general, the compositions of the present disclosure may be spun into fibers and incorporated into various textiles for a number of end uses. In some embodiments, the device is a textile used for donor organ preservation. In some embodiments, diabetic socks capable of releasing nitric oxide may be used to improve circulation in diabetic patients. In some embodiments, bedding capable of releasing nitric oxide may be used to aid in the prevention of bed sores.

Medical devices of the present disclosure may be used externally or internally. Illustrative external uses for medical devices and articles containing the compositions of the present disclosure include, for example, hair growth, increased circulation and donor organ preservation. As a first example, a hat may include the compositions of the present disclosure in order to release nitric oxide to the scalp to stimulate hair growth. The topical hair loss medication minoxidil is a potent vasodilator. Compositions of the present disclosure may function in a similar manner by releasing nitric oxide to the scalp. Likewise, diabetic socks, textiles, and other articles of clothing may be used to provide nitric oxide to the skin. Diabetic patients are particularly known to have poor circulation and low nitric oxide levels, and diabetic socks and other articles of clothing containing the compositions described herein may be beneficial in treating these and other patients having poor circulation. As previously mentioned, textiles containing compositions of the present disclosure may be used to wrap an organ for preservation during transplant operations.

Other embodiments of the invention utilize electrospun fibers formed from compositions of the invention in textiles and fabrics that could used in items like handkerchiefs, bedsheets and the like, which may be use to deliver nitric oxide to a patient.

In some embodiments, medical devices of the present disclosure may be used for either short-term or long-term release of nitric oxide. For example, some cardiovascular applications may require a high NO release rate immediately after a stent or vascular graft is implanted, followed by a sustained, lower NO release rate thereafter. In other embodiments, a sustained low level of NO release may be preferred, however. Compositions of the present disclosure may be specifically tailored to meet either of these types of NO release criteria.

Medical devices of the present disclosure may be used to treat, mediate or prevent a variety of diseases in which nitric oxide is implicated as having a functional role. Such diseases include, for example, infection, diabetic neuropathy, hypertension, sexual dysfunction, cancer, deep vein thrombosis, tendinopathy, and Duchenne muscular dystrophy. In some embodiments, the compositions and medical devices of the present disclosure may replace or be used in combination with traditional anti-coagulant drugs and therapies.

Benefits of the compositions described herein are embodied by nitric oxide-releasing bandages. Preliminary studies on isolated rat hearts have demonstrated increased coronary flow upon exposure to a bandage containing the nitric-oxide releasing materials of the present disclosure.

In other various embodiments, methods for preparing compositions for controlled release of nitric oxide are described herein. The methods include providing a polymer solution of a biodegradable polymer dissolved in a solvent; dispersing a nitric oxide-releasing material into the polymer solution; and electrospinning the polymer solution into a fiber containing pores. For example, in some embodiments, the nitric oxide releasing material is a diazeniumdiolate. In some embodiments, the methods further include annealing the fiber by heating. Such annealing may be used to densify the porous structure of the fibers and further encapsulate the nitric oxide-releasing material contained therein, thereby prolonging the NO release time.

In other various embodiments of methods for preparing compositions for controlled release of nitric oxide, the methods include providing a polymer solution of a biodegradable polymer dissolved in a solvent; dispersing a porous material in the polymer solution; electrospinning the polymer solution into a fiber containing pores; and impregnating the porous material with nitric oxide. The porous material may be, for example, a zeolite, a metal-organic framework, or mesoporous molecular sieve. In some embodiments, the methods further include annealing the fiber by heating after impregnating the porous material with nitric oxide.

Experimental Examples

The following examples are provided to more fully illustrate some of the embodiments disclosed hereinabove. It should be appreciated by those of ordinary skill in the art that the techniques disclosed in the examples that follow represents techniques that constitute illustrative modes for practice of the disclosure. Those of ordinary skill in the art should, in light of the present disclosure, appreciate that many changes can be made in the specific embodiments that are disclosed and still obtain a like or similar result without departing from the spirit and scope of the disclosure.

Example 1

Preparation of a Fiber Containing Diazeneiumdiolates

Porous poly(lactic acid) polymer fibers containing a diazeniumdiolate were prepared by electrospinning. High molecular weight poly(lactic acid) (~100 kDa) was dispersed in chloroform at room temperature at a concentration of 7-10% w/w to produce a viscous polymer solution. A diazeniumdiolate was then introduced into the polymer solution in varying quantities. Electrospinning was thereafter initiated by feeding the polymer solution into a syringe containing an attached 18 to 22 gauge needle. A flow rate of 1 mL/hr was used. A voltage of 15-20 kV was applied to the needle using a variable high voltage power supply during electrospinning. Aligned fibers containing the diazeniumdiolate were obtained by using a grounded rotating drum positioned a distance of 25 cm from the needle tip. A flat piece of aluminum foil (15 cm×15 cm) was used for collecting random fibers.

Example 2

Synthesis of Zeolite-A and Nanoscale Zeolite-A

Sodium hydroxide (0.723 g) was first dissolved in 80 mL of DI water and then divided into two equal portions. One half of the sodium hydroxide solution was combined with sodium aluminate (8.258 g) and stirred at room temperature (RT) until clear. The second half of the sodium hydroxide solution was mixed with sodium metasilicate (15.48 g) at RT until a clear solution resulted. These clear solutions were then combined with stirring at RT, resulting in a thick white gel. The gel was further stirred until homogenous and then transferred to a 150 mL polypropylene bottle before being subsequently heated for 24 h at 90° C. The resulting white precipitate was washed repeatedly with 10 mL aliquots of deionized water and isolated through centrifugation.

Nanoscale Zeolite-A was synthesized as follows: Aluminum isopropoxide (0.75 g), trimethyl ammonium hydroxide (5.0 g), 1 M sodium hydroxide solution (0.58 mL) and 7 mL of DI water were stirred together until clear in a polypropylene bottle at 40° C. In a separate polypropylene bottle, 30% silica sol (2.25 g) was combined with 2.0 mL of DI water and stirred under at 40° C. until clear. The solutions were then combined and placed in an oven for 24 h at 80° C. The resulting solution was a suspension of zeolite nanoparticles, which was washed repeatedly with a water/ethanol mixture and isolated by centrifugation. After repeated washings and centrifugation of the solution, the zeolites eventually became visible as a white precipitate. When the white precipitate formed, several more washes and centrifugations were performed to separate the zeolite from the supernatant liquid. Drying of the isolated zeolite was conducted overnight at 90° C. under reduced pressure.

Example 3

Preparation of Cobalt (II)-Exchanged Zeolite-A and Cobalt (II)-Exchanged Nanoscale Zeolite-A Cobalt (II)-exchanged zeolite A was prepared by combining Zeolite-A (1 g) in a 0.05 M solution of cobalt (II) acetate (100 mL) with stirring at RT for at least 24 hours. The zeolite was isolated through centrifugation, followed by two more washing and centrifugation steps before the cobalt (II)-exchanged Zeolite-A was dried overnight at 80-90° C. under reduced pressure. Elemental analysis of the cobalt (II)-exchanged Zeolite-A by ICP showed 9.27 wt. % cobalt. Both cobalt (II)-exchanged Zeolite-A and cobalt (II)-exchanged nanoscale Zeolite-A were prepared by the aforesaid method.

Figure 4A:
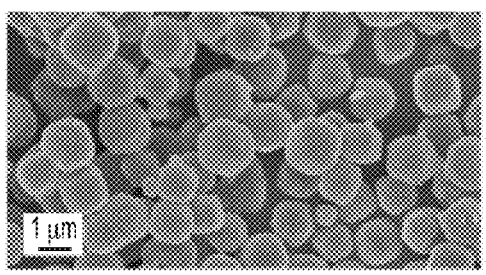
FIG. 4A shows an illustrative SEM image of cobalt (II)-exchanged Zeolite-A.
Figure 4B:
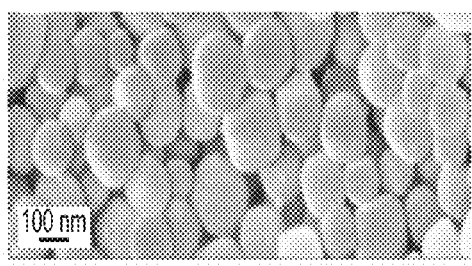
FIG. 4B shows an illustrative SEM image of cobalt (II)-exchanged nanoscale Zeolite-A.

FIG. 4A shows an illustrative SEM image of cobalt (II)-exchanged Zeolite-A. FIG. 4B shows an illustrative SEM image of cobalt (II)-exchanged nanoscale Zeolite-A. As demonstrated from FIGS. 4A and 4B, cobalt (II)-exchanged Zeolite-A had particle sizes ranging from ~1-2 μm, whereas cobalt (II)-exchanged nanoscale Zeolite-A had particle sizes averaging ~100 nm. Both cobalt (II)-exchanged zeolites were dark blue when infused with NO. The dark blue color faded to pink upon exposure of the NO-loaded zeolites to atmospheric moisture. NO release rates of the zeolites are considered in more detail hereinbelow.

Example 4

Preparation of a Fiber Containing Cobalt (II)-Exchanged Zeolite-A

Figure 5:
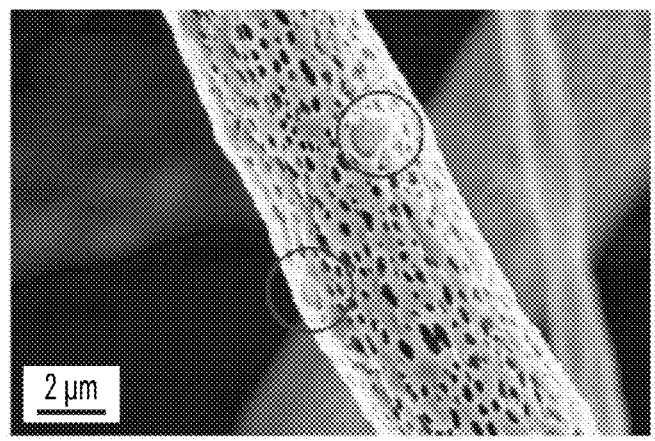
FIG. 5 shows an illustrative SEM image of a cobalt (II)-exchanged Zeolite-A-containing fiber.
Figure 6:
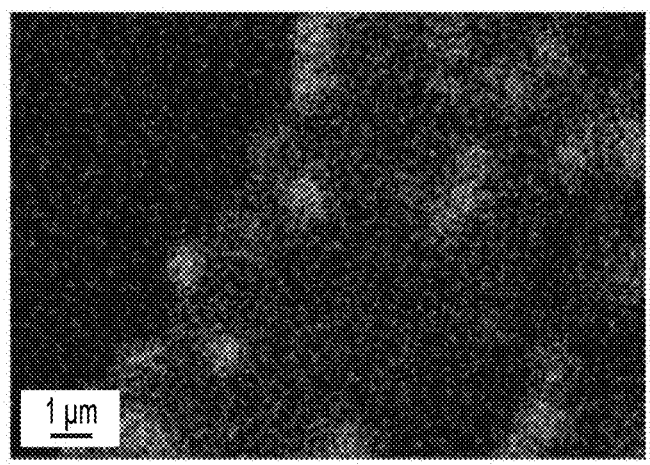
FIG. 6 shows an illustrative EDAX silicon map showing that the zeolite particles are well dispersed throughout a cobalt (II)-exchanged Zeolite-A-containing fiber with little to no particle aggregation.
Figure 7:
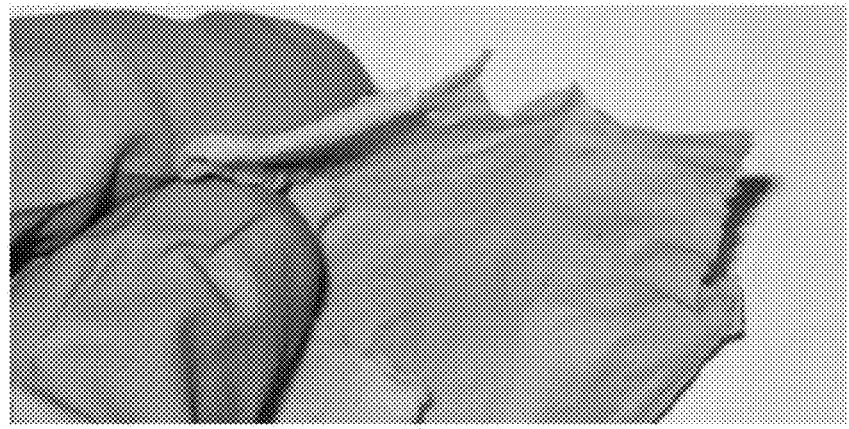
FIG. 7 shows an illustrative image of a bandage formed from a plurality of cobalt (II)-exchanged Zeolite-A-containing fibers.

Aligned porous poly(lactic acid) polymer fibers containing cobalt (II)-exchanged Zeolite-A were prepared by electrospinning A solution of 1.50 g of poly(lactic acid) in 10 mL of dry chloroform was first prepared. Thereafter, a dry powder of cobalt (II)-exchanged Zeolite-A (0.2 g) was sonicated in 500 mL of chloroform until the zeolite crystals were well dispersed. This suspension was then mixed with the above poly (lactic acid) solution with stirring, resulting in a blue viscous polymer solution. The viscous solution was then fed through a 20-gauge needle at a rate of 0.20-0.25 mL/h. To initiate electrospinning, a voltage of 10 kV was applied to the needle using a variable high voltage power supply. Aligned fibers were collected using a grounded rotating drum covered with aluminum foil positioned at a distance of 20 cm from the needle tip. FIG. 5 shows an illustrative SEM image of a cobalt (II)-exchanged Zeolite-A-containing fiber. The porous structure of the electrospun fiber is clearly observable in the image. FIG. 5 also shows that a few of the zeolite crystals migrate to the surface of the fiber. FIG. 6 shows an illustrative EDAX silicon map showing that the zeolite particles are well dispersed throughout the cobalt (II)-exchanged Zeolite-A-containing fiber with little to no particle aggregation. In FIG. 6, concentrated brighter areas correspond to detected silicon, which is diagnostic of the zeolite. FIG. 7 shows an illustrative image of a bandage formed from a plurality of cobalt (II)-exchanged Zeolite-A-containing fibers. Comparable results were obtained from fibers containing cobalt (II)-exchanged nanoscale Zeolite-A, although such fibers were somewhat more prone to zeolite aggregation within the fiber, resulting in beaded fibers in some cases.

Example 5

Nitric Oxide Loading of Cobalt (II)-Exchanged Zeolite-A

After electrospinning, the fibers containing cobalt (II)-exchanged Zeolite-A were placed in a pressure vessel and dried at approximately 40° C. overnight under vacuum in an oven. Bluish fibers were obtained. The pressure vessel was then purged with argon for 15-20 minutes, and the fibers were then exposed to nitric oxide (4 atm) for 1 hour. The excess nitric oxide was removed, and the pressure vessel was again purged with argon thereafter. Fibers containing cobalt (II)-exchanged Zeolite-A were charged with nitric oxide in a similar manner. The bare cobalt (II)-exchanged Zeolite-A was loaded with nitric oxide similarly, except the zeolite was dried under vacuum overnight at 90° C. prior to loading.

Example 6

Annealing of NO-Loaded Fibers Containing Cobalt (II)-Exchanged Zeolite-A

After being loaded with NO, the fibers from Example 5 were immediately placed in an oven at 65° C. for 30 minutes, followed by 10 minutes of cooling to RT. This process was repeated three times. After the last heating cycle, the pressure vessel was again purged with argon to expel any excess or desorbed nitric oxide resulting from annealing. FIG. 8 shows an illustrative cross-sectional SEM image of a cobalt (II)-exchanged Zeolite-A-containing fiber following NO loading and annealing. The porous structure of the fiber exterior remains clearly observable in the image, but the inner pores were observed to be coalesced and densified by the annealing process. In contrast, a cross-sectional SEM image obtained after freeze fracturing of a non-annealed fiber clearly showed the presence of an internal pore structure.

Example 7

Quantification of NO Release from Cobalt (II)-Exchanged Zeolite-A, Non-Annealed Porous Fibers Containing Cobalt (II)-Exchanged Zeolite-A, and Annealed Fibers Containing Cobalt (II)-Exchanged Zeolite-A All samples were quantified for NO release immediately after NO infusion or following annealing. Nitric oxide release was stimulated by exposing the sample to a moisture-rich gas flow. Constant relative humidity was achieved by passing an argon flow through a saturated solution of magnesium chloride before exposure to the sample. This gas flow maintained a constant 33% relative humidity. The flow rate was 180 cc/min. The evolved NO was carried by the argon gas into a vessel containing 10 mL of deionized water, where nitric oxide reacted to form nitrite ions. NO quantification was conducted by analyzing for produced nitrite using the Griess Reagent.

Cobalt (II)-Exchanged Zeolite-A:

FIG. 9A shows an illustrative NO release profile from NO-loaded cobalt (II)-exchanged Zeolite-A. FIG. 9B shows an illustrative NO release profile from NO-loaded cobalt (II)-exchanged nanoscale Zeolite-A. FIGS. 9A and 9B show that most of the NO contained within the zeolites was released within the first 100 seconds following exposure to moisture. As determined from the NO release profiles, the NO loading capacity of cobalt (II)-exchanged Zeolite-A was 0.774 mmol NO/g zeolite, and for the cobalt (II)-exchanged nanoscale Zeolite-A the NO loading capacity was ~0.85 to 0.90 mmol NO/g zeolite.

Non-Annealed, Porous Fibers Containing Cobalt (II)-Exchanged Zeolite-A:

FIG. 10 shows illustrative NO release profiles from non-annealed, porous fibers containing cobalt (II) exchanged Zeolite-A 10 and cobalt (II) exchanged nanoscale Zeolite-A 11. The NO release profiles in both cases were similar to the free zeolites, with most of the NO being released during the first 100 seconds following exposure to moisture. Although the NO release profiles were not significantly altered for the non-annealed, porous fibers, the presence of the polymer binder places the nitric oxide-releasing material in a form more compatible for biological and medical device applications.

The NO storage capacity of the cobalt (II)-exchanged Zeolite-A in the fibers was slightly lower than that of the corresponding free zeolite without the polymer (0.55 mmol NO/gram zeolite versus 0.775 mmol NO/gram zeolite for cobalt (II)-exchanged Zeolite-A and 0.75 mmol NO/gram zeolite versus ~0.85 mmol NO/gram zeolite for cobalt (II) exchanged nanoscale Zeolite-A). The reduced NO storage capacity may have been a byproduct of the electrospinning process or NO loading of the zeolites contained within the polymer fiber.

Figure 11A:
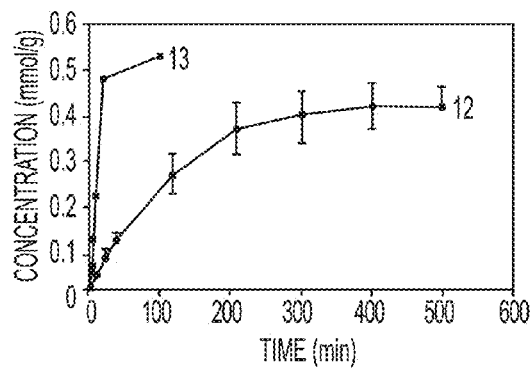
FIGS. 11A and 11B show illustrative NO release profiles from annealed fibers containing cobalt (II)-exchanged Zeolite-A and cobalt (II)-exchanged nanoscale Zeolite-A.
Figure 11B:
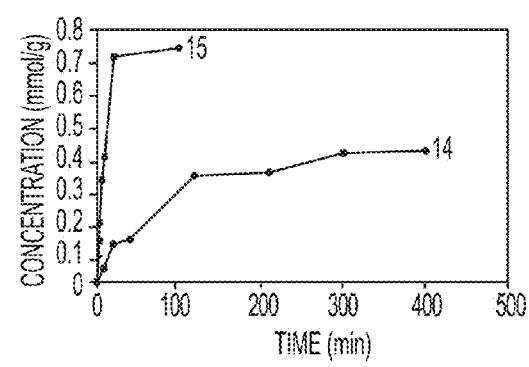
Figure 12:
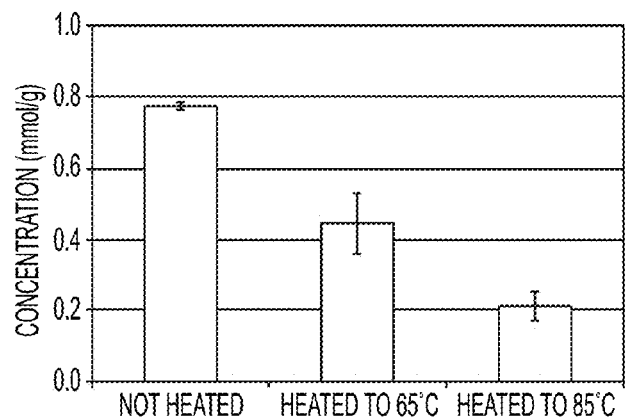
FIG. 12 shows a histogram showing an illustrative decrease in NO loading in cobalt (II)-exchanged Zeolite-A-containing fibers annealed at 65° C. and 85° C.

Annealed Fibers Containing Cobalt (II)-Exchanged Zeolite-A:

FIGS. 11A and 11B show illustrative NO release profiles from annealed fibers containing cobalt (II)-exchanged Zeolite-A 12 and cobalt (II)-exchanged nanoscale Zeolite-A 14, each in comparison to non-annealed fibers 13 and 15 containing the same zeolite material. As shown in FIGS. 11A and 11B, annealing resulted in a considerably more prolonged release of NO from the fibers, as well as a slower rate of initial NO release. Although NO release was more prolonged in the annealed fibers, overall NO loading was reduced. FIG. 12 shows a histogram showing an illustrative decrease in NO loading in cobalt (II)-exchanged Zeolite-A-containing fibers annealed at 65° C. and 85° C. The NO loading dropped by about 40% in the fibers annealed at 65° C., whereas the NO loading dropped by about 75% when annealing was conducted at 85° C.

Example 8

Figure 13:
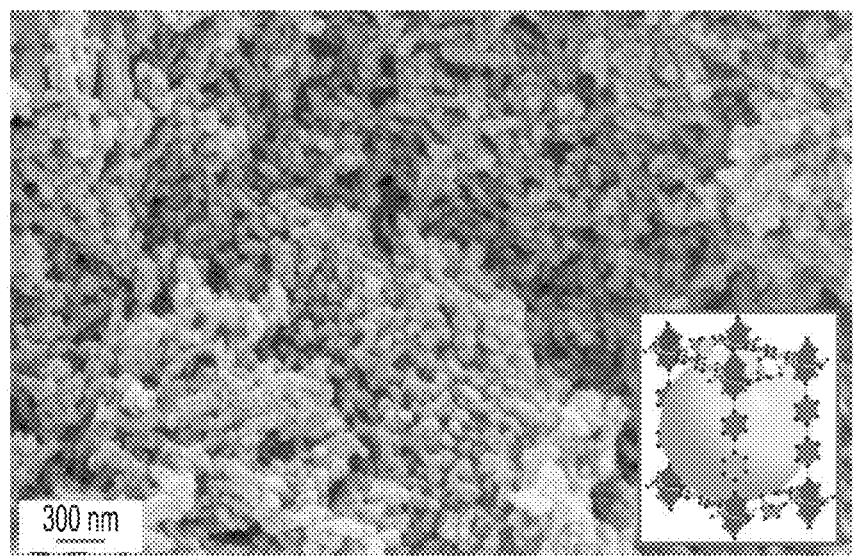
FIG. 13 shows an illustrative SEM image of as-synthesized copper (II) biphenyl-4,4'-dicarboxylic acid triethylenediamine metal-organic framework.

Synthesis of a Copper (II) Biphenyl-4,4'-Dicarboxylic Acid Triethylenediamine Metal-Organic Framework Cu (II) metal-organic framework nanocrystals were synthesized in gram quantities by modifying published procedures to control the water content in the reaction mixture, to reduce the synthesis time, and to improve reproducibility. In a typical synthesis, a 100 mL ethanol solution containing 1.75 g (8.8 mmol) of copper (II) acetate monohydrate was stirred at room temperature until dissolved. Then, 30 g of activated 4 Å (4-8 mesh) molecular sieves were added to the solution. After drying for 1 h, the molecular sieves were removed and the solution was capped for further use. A second solution consisting of 1.05 g (9.20 mmol) of triethylenediamine (TED) in 90 mL of toluene was dried with 10 g of activated 4 Å (4-8 mesh) molecular sieves. After drying for 1 h, the molecular sieves were removed. A third solution made of 2.00 g (8.60 mmol) of biphenyl-4,4'-dicarboxylic acid (BPDA) and 2.6 mL of formic acid in 200 mL of DMF was heated to 110° C. in a 500 mL round bottom flask until the BPDA was dissolved. The solution was then cooled to room temperature. To remove the excess of water introduced by the formic acid, 1.5 g of activated 4 Å(4-8 mesh) molecular sieves was added to the solution. After drying for 1 h, the molecular sieves were removed and the solution was refluxed at 110° C. with strong agitation until the BPDA dissolved. Once the DMF solution reached 110° C., the ethanol solution was added all at once and was immediately followed by addition of the toluene solution. The final solution was heated to 110° C. with refluxing and stirring for 30 h with the condenser open to atmosphere. The resulting blue solution was then cooled to room temperature. Nanocrystalline metal-organic framework material obtained by filtering the blue solution and then washing the blue cake with 3×50 mL of DMF. The cake was dried for 1 d at 80° C. in a vacuum oven. Activated metal-organic framework nanocrystals were obtained by filtering and washing the cake with a continuous flow of 3×50 mL each of DMF, $CHCl_3$, acetone, and $CHCl_3$ in that order. The activated material was dried in a vacuum oven at 90° C. for 1 d and then cooled to room temperature under a blanket of nitrogen before being removed from the vacuum oven. Activated metal organic framework nanocrystals (2.8 g) were recovered and stored in a capped vial filled with nitrogen. FIG. 13 shows an illustrative SEM image of as-synthesized copper (II) biphenyl-4,4'-dicarboxylic acid triethylenediamine metal-organic framework. BET surface areas of approximately 3000 $m^2/g$ and a pore size of 0.9 nm were calculated by analysis of the adsorption isotherms. Thermogravimetric analysis indicated stability up to 300° C.

Example 9

Nitric Oxide Loading of Copper (II) Biphenyl-4,4'-Dicarboxylic Acid Triethylenediamine Metal-Organic Framework Nitric oxide loading of the metal-organic framework nanocrystals or fibers containing the metal-organic framework nanocrystals were conducted similarly to that of the Co (II)-exchanged Zeolite A. Briefly, the metal-organic framework nanocrystals or fibers containing the metal-organic framework nanocrystals were dehydrated in a pressure vessel for 3 h at 60° C. under vacuum. The vessel was then purged with Ar flow for 30 minutes and then backfilled with 4 atm of NO for 1 hour. After 1 h, the vessel was again evacuated and excess NO was flushed out of the vessel by purging with Ar for 1 h. Samples were kept in the pressure vessel until ready to be used for analysis.

Example 10

Figure 14:
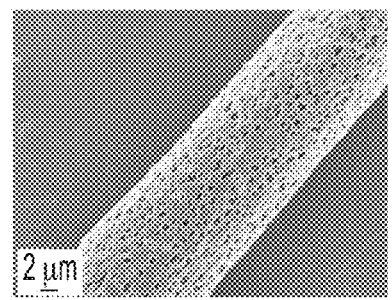
FIG. 14 shows an illustrative SEM image of a fiber containing copper (II) biphenyl-4,4'-dicarboxylic acid triethylenediamine metal-organic framework nanocrystals.

Quantification of NO Release from Fibers Containing Copper (II) Biphenyl-4,4'-Dicarboxylic Acid Triethylenediamine Metal-Organic Framework Nanocrystals Fibers containing copper (II) biphenyl-4,4'-dicarboxylic acid triethylenediamine metal-organic framework nanocrystals were prepared by electrospinning similarly to the process described in Example 4. FIG. 14 shows an illustrative SEM image of a fiber containing copper (II) biphenyl-4,4'-dicarboxylic acid triethylenediamine metal-organic framework nanocrystals. As shown in FIG. 14, the fibers containing the metal-organic framework was substantially similar in appearance to the fibers containing the zeolite.

Figure 15:
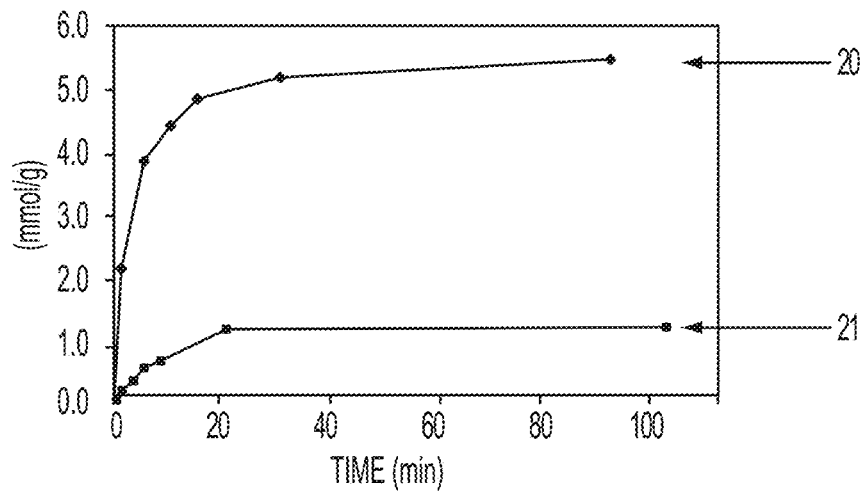
FIG. 15 shows illustrative comparative NO release profiles for non-annealed fibers containing copper (II) biphenyl-4,4'-dicarboxylic acid triethylenediamine metal-organic framework nanocrystals and cobalt (II)-exchanged nanoscale Zeolite-A.

Quantification of NO release was conducted using moist Ar in a manner analogous to that described in Example 7, except a saturated manganese chloride solution was used to maintain 50% relative humidity. FIG. 15 shows illustrative comparative NO release profiles for non-annealed fibers containing copper (II) biphenyl-4,4'-dicarboxylic acid triethylenediamine metal-organic framework nanocrystals 20 and cobalt (II)-exchanged nanoscale Zeolite-A 21. As shown in FIG. 15, under the conditions tested, the NO release capacity for the metal-organic framework was about 5 times that of the cobalt (II)-exchanged nanoscale Zeolite-A. The NO storage capacity of the metal-organic framework-containing fibers was approximately 5 mmol NO/gram metal-organic framework. The higher NO storage capacity can be attributed to the higher surface area present in the metal-organic framework compared to the zeolite. Nitric oxide release was complete in about 40 minutes. Note that the fibers of FIG. 15 were non-annealed, so the NO release rate was more rapid than was observed for annealed fibers in FIGS. 11A and 11B.

Example 11

Influence of NO-Releasing Fibers on Rat Heart Arterial Blood Flow

Figure 16:
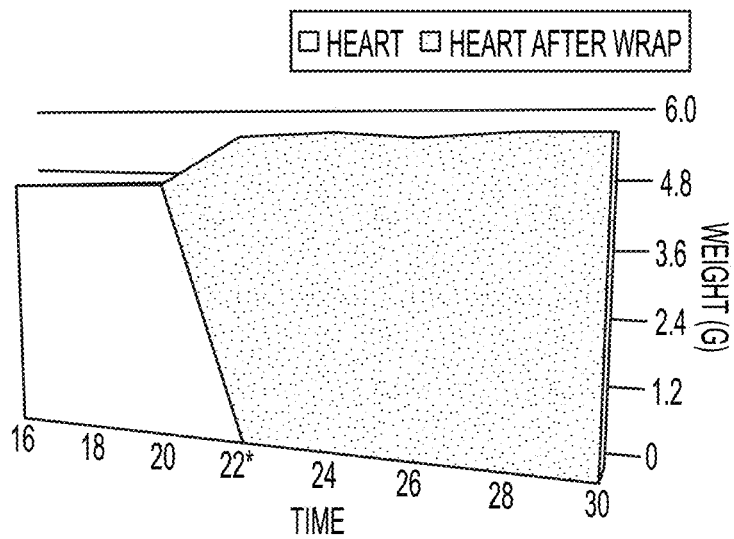
FIG. 16 shows a plot demonstrating an illustrative increase in coronary flow following exposure of the heart to the nitric oxide-releasing bandage.

A bandage fabricated from fibers containing a nitric oxide-releasing metal-organic framework was prepared as outlined above. After animal sacrifice, rat hearts were immediately excised from the chest cavity and cannulated through the aorta, where it was fastened with a silk tie. The heart was then perfused at a constant hydrostatic pressure of 50 mm Hg with Kreb's buffer at 37° C., which was continually gassed with 95% $O_2$ and 5% $CO_2$. After perfusion, the heart was placed in a warming jacket at 37° C. The buffer was flowed through the coronary arteries and collected in a fraction collector at one-minute intervals. Each fraction was then weighed to calculate the coronary flow rate. Following establishment of a baseline flow rate for 20 minutes, the warming jacket was removed, and a nitric oxide-releasing bandage was wrapped around the heart. The warming jacket was subsequently reapplied. The buffer flow was allowed to equilibrate for 10 minutes, and fraction collection was then conducted as above. FIG. 16 shows a plot demonstrating an illustrative increase in coronary flow following exposure of the heart to the nitric oxide-releasing bandage. As shown in FIG. 16, the coronary flow rate increased significantly after wrapping the heart with the nitric oxide-releasing bandage.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. A composition for controlled release of nitric oxide, comprising:
   an aligned electrospun, porous fiber, wherein the fiber comprises a porous biodegradable polymer that comprises pores; and a nitric oxide-releasing material that is at least partially encapsulated by the biodegradable polymer, wherein the nitric oxide-releasing material is located within the pores of the biodegradable polymer fiber; and
   a second polymer, wherein the second polymer forms a layer over the fiber and wherein the second polymer does not contain nitric oxide-releasing material.

2. The composition of claim 1, wherein the porous biodegradable polymer is poly(lactic acid).

3. The composition of claim 1, wherein the nitric oxide-releasing material is a diazeniumdiolate.

4. The composition of claim 1, wherein the biodegradable polymer is hydrolysable in an aqueous solution; and
   wherein a monomer produced by hydrolysis of the biodegradable polymer is operable for buffering the aqueous solution.

5. The composition of claim 1, wherein the nitric oxide-releasing material comprises nitric oxide contained within a zeolite.

6. The composition of claim 5, wherein the zeolite is cobalt (II)-exchanged Zeolite-A.

7. The composition of claim 1, wherein a plurality of the electrospun, porous fibers are assembled into a free-standing paper.

8. The composition of claim 7, wherein the fibers have diameters between about 100 nm and about 25 μm.

9. The composition of claim 1, wherein the nitric oxide-releasing material is nitric oxide contained within a metal-organic framework.

10. A medical device comprising the composition of claim 1.

11. The medical device of claim 10, wherein the nitric oxide-releasing material is a diazeniumdiolate.

12. The medical device of claim 10, wherein the nitric oxide-releasing material is nitric oxide contained within a zeolite.

13. The medical device of claim 10, wherein the nitric oxide-releasing material is nitric oxide contained within a metal-organic framework.

14. The medical device of claim 10, wherein the composition coats the surface of the medical device.

15. The medical device of claim 10, wherein the medical device is selected from the group consisting of stents, vascular grafts, pacemaker leads, heart valves, electrodes, sensors, trocars, guide wires, catheters, ocular lenses, sling materials, sutures, wound dressing and bandages, blood collection bags and storage tubes, tubing for blood transfusions and hemodialysis, diabetic socks, and bedding.

16. The medical device of claim 10, wherein the medical device is a textile.

17. The medical device of claim 10, wherein the medical device is a bandage.

18. A method for preparing a composition for controlled release of nitric oxide, said method comprising:
   a) providing a polymer solution comprising a biodegradable polymer dissolved in a solvent;
   b) dispersing a nitric oxide-releasing material in the polymer solution; and
   c) electrospinning the polymer solution into an aligned electrospun, porous fiber that contains pores and a nitric oxide-releasing material that is at least partially encapsulated by the biodegradable polymer, wherein nitric oxide-releasing material is located within the pores of the biodegradable polymer fiber; and
   d) coating the aligned electrospun, porous fiber with a polymer layer, said polymer layer comprising a biodegradable polymer does not contain the nitric oxide-releasing material.

19. The method of claim 18, wherein the nitric oxide-releasing material is a diazeniumdiolate.

20. The method of claim 18, further comprising:
   annealing the aligned electrospun, porous fiber by heating prior to coating the aligned electrospun, porous fiber.

21. A method for preparing a composition for controlled release of nitric oxide, said method comprising:
   a) providing a polymer solution comprising a biodegradable polymer dissolved in a solvent;
   b) dispersing a porous material in the polymer solution; wherein the porous material is selected from the group consisting of a zeolite and a metal-organic framework;
   c) electrospinning the polymer solution to form an aligned electrospun, porous fiber that contains pores and said porous material that is at least partially encapsulated by the biodegradable polymer, wherein porous material is located within the pores of the biodegradable polymer fiber;

d) impregnating the porous material with nitric oxide; and e) coating the aligned electrospun, porous fiber with a polymer layer, said polymer layer comprising a biodegradable polymer does not contain the nitric oxide-releasing material.

22. The method of claim 21, further comprising:

annealing the aligned electrospun, porous fiber by heating after said impregnating step.

* * * * *

UNITED STATES PATENT AND TRADEMARK OFFICE
CERTIFICATE OF CORRECTION

PATENT NO. : 9,216,198 B2  
APPLICATION NO. : 12/750317  
DATED : December 22, 2015  
INVENTOR(S) : Kenneth J. Balkus et al.

Page 1 of 1

It is certified that error appears in the above-identified patent and that said Letters Patent is hereby corrected as shown below:

IN THE SPECIFICATION

Column 2,
Lines 16-21, "($NaAlSi_2O_6.H_2O$), chabazite [$(Ca,Na_2,K_2,Mg)Al_2Si_4O_{12}.6H_2O$], clinoptilolite [$(Na,K,Ca)_{2-3}Al_3(Al,Si)_2Si_{13}O_{36}.12(H_2O)$], heulandite [$(Ca,Na)_{2-3}Al_3(Al,Si)_2Si_{13}O_{36}.12H_2O$], natrolite ($Na_2Al_2Si_3O_{10}.2H_2O$), phillipsite [$(Ca,Na_2,K_2)_3Al_6Si_{10}O_{32}.12H_2O$], and stilbite ($NaCa_2Al_5Si_{13}O_{36}.14H_2O$)." should read
--($NaAlSi_2O_6 \cdot H_2O$), chabazite [$(Ca,Na_2,K_2,Mg)Al_2Si_4O_{12} \cdot 6H_2O$], clinoptilolite [$(Na,K,Ca)_{2-3}Al_3(Al,Si)_2Si_{13}O_{36} \cdot 12(H_2O)$], heulandite [$(Ca,Na)_{2-3}Al_3(Al,Si)_2Si_{13}O_{36} \cdot 12H_2O$], natrolite($Na_2Al_2Si_3O_{10} \cdot 2H_2O$), phillipsite [$(Ca,Na_2,K_2)_3Al_6Si_{10}O_{32} \cdot 12H_2O$], and stilbite ($NaCa_2Al_5Si_{13}O_{36} \cdot 14H_2O$).--.

Signed and Sealed this
Twelfth Day of April, 2016

Michelle K. Lee
*Director of the United States Patent and Trademark Office*